United States Patent [19]

Duncan

[11] Patent Number: 5,086,774
[45] Date of Patent: Feb. 11, 1992

[54] SYSTEM AND METHOD FOR AUTOMATICALLY COMPENSATING FOR LATENCY CONDUCTION TIME IN A PROGRAMMABLE PACEMAKER

[75] Inventor: James L. Duncan, Alpharetta, Ga.

[73] Assignee: Siemens-Pacesetter, Inc., Sylmar, Calif.

[21] Appl. No.: 503,209

[22] Filed: Apr. 2, 1990

[51] Int. Cl.$^5$ .............................................. A61W 1/00
[52] U.S. Cl. ............................................. 128/419 PG
[58] Field of Search ...................... 128/419 P, 419 PG

[56] References Cited

U.S. PATENT DOCUMENTS

| | | | |
|---|---|---|---|
| 4,429,697 | 2/1984 | Nappholz et al. | 128/419 PG |
| 4,686,988 | 8/1987 | Sholder | 128/419 PT |
| 4,712,555 | 12/1987 | Thornander et al. | 128/419 PG |
| 4,714,079 | 12/1987 | Hedberg et al. | 128/419 PG |
| 4,815,469 | 3/1989 | Cohen et al. | 128/634 |
| 4,856,523 | 8/1989 | Sholder et al. | 128/419 PG |
| 4,920,965 | 5/1990 | Funke et al. | 128/419 PG |
| 4,945,909 | 8/1990 | Fearnot et al. | 128/419 PG |

OTHER PUBLICATIONS

Catania, et al., "AV Delay Latency Compensation", *J. of Electrophys.*, vol. 1, No. 3, pp. 242–249 (1987).
Ausubel et al., "Interatrial Conduction During Cardiac Pacing", *Pace*, vol. 9, pp. 1026–1031 (Nov./Dec. 1986, Part II).
Wish et al., "Importance of Left Atrial Timing in the Programming of Dual-Chamber Pacemakers", *Am. J. of Cardiol.*, vol. 60, pp. 556–571, Sep. 1987.
Alt et al., "Different Beneficial AV Intervals with DDD Pacing After Sensed or Paced Atrial Events", *J. of Electrophys.*, vol. 1, No. 3, pp. 250–256 (1987).

Primary Examiner—Francis Jaworski
Assistant Examiner—George Manuel
Attorney, Agent, or Firm—Bryant R. Gold; Malcolm J. Romano

[57] ABSTRACT

An implantable pacemaker provides a paced AV delay that is automatically adjusted to include patient variations in latency conduction, that is, the time interval between a stimulus to the heart and an evoked potential, time due to lead position and specific patient latency. An AV timer, designed to provide a programmed AV interval, starts its timing operation at the generation of an atrial pulse, and restarts the timing operation again at the occurrence of the evoked atrial potential. The evoked atrial potential is typically monitored from a ring electrode of a bipolar lead relative to the pacemaker can (case), although other monitoring configurations are also possible. The length of the AV intrval is programmed to a desired value using conventional programming techniques. By starting the AV timer from the paced atrial stimulus, and restarting it from the evoked atrial potential, all variablility in nodal conduction time due to lead position and specific patient latency is removed, thereby obviating the need of having the pacemaker make adjustments to the AV interval. The paced AV delay (the time interval from the generation of an atrial stimulus to the generation of a ventricular stimulus) is automatically adjusted to compensate for these variations, while the AV interval (desired time from an atrial depolarization to a ventricular depolarization) remains at the desired value. In a rate-responsive packemaker, the programmed AV interval may still be shortened to mimic decreases in AV nodal conduction during periods of physical activity without affecting operation of the invention.

16 Claims, 3 Drawing Sheets

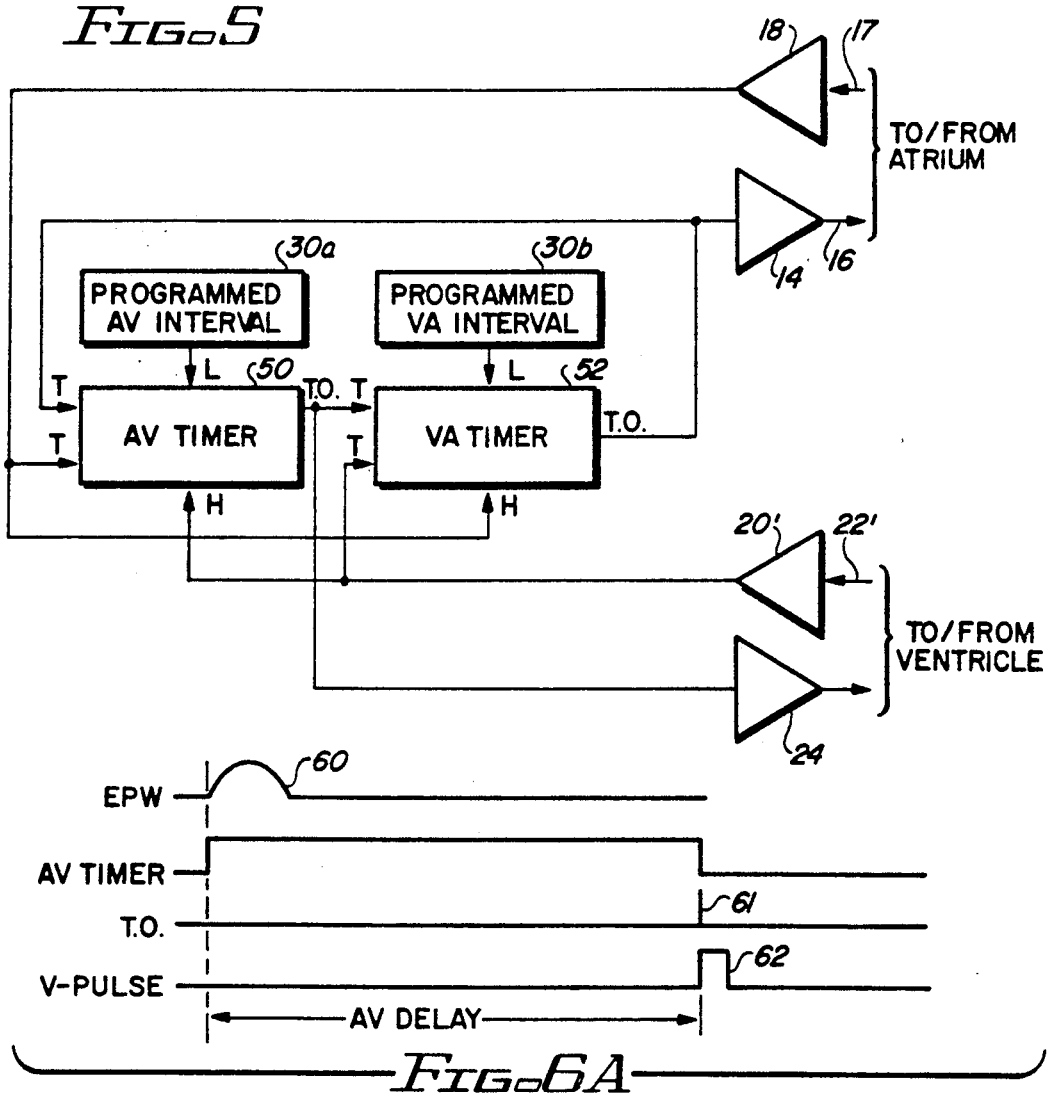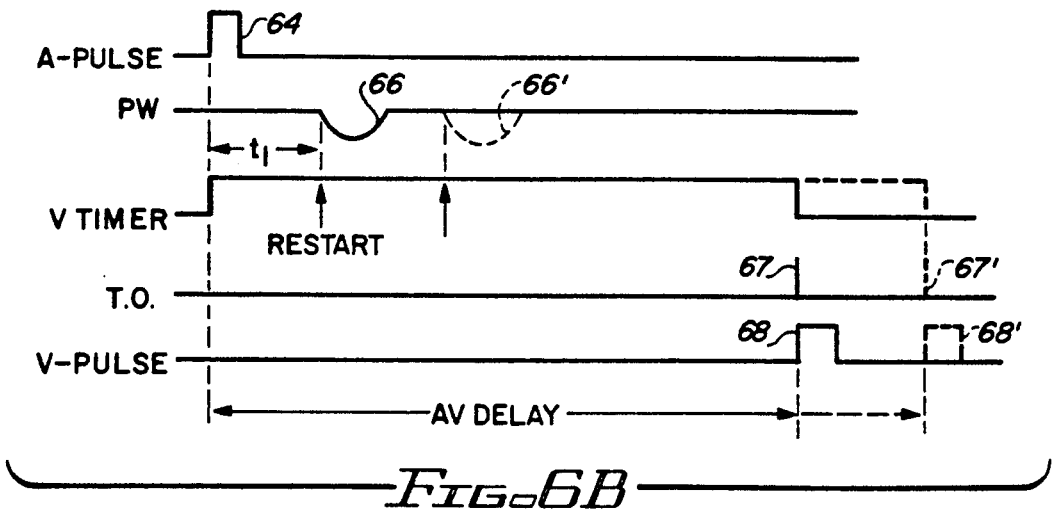

SYSTEM AND METHOD FOR AUTOMATICALLY COMPENSATING FOR LATENCY CONDUCTION TIME IN A PROGRAMMABLE PACEMAKER

BACKGROUND OF THE INVENTION

The present invention relates to implantable pacemakers, and more particularly to an implantable pacemaker wherein the paced AV delay is automatically adjusted based on the timing of the atrial-evoked potential.

The paced AV delay of an implantable pacemaker is the time interval between application of an electrical stimulus to the atrium (A-pulse) and the application of an electrical stimulus to the ventricle (V-pulse). The AV delay represents the best estimate of the nodal conduction time in the patient's heart as a stimulus travels from the atria to the ventricles. That is, the AV delay represents an estimate of the optimum time between atrial depolarization and ventricular depolarization.

Early demand pacemakers employed a timer circuit that generated a fixed AV interval (AVI) that was triggered by the generation of an A-pulse or by the sensing of atrial depolarization (P-wave). If ventricular depolarization (an R-wave) was not sensed before the termination of the AVI, a ventricular stimulus (V-pulse) was generated. In this manner, the fixed AVI of the pacemaker represented the maximum allowable time between depolarization of the atria and depolarization of the ventricles.

With the advent of programmable demand pacemakers, it became advantageous to make the AVI of the pacemaker a programmable value. This is because the optimum AV delay, i.e., the time delay between atrial and ventricular depolarization, varies greatly between different patients. Further, the optimum AV delay for a given patient may vary widely depending upon various factors, including whether the patient is being administered drugs, the heart rate (e.g., level of exercise) of the patient, etc. Thus, being able to set the AVI of the pacemaker to a desired value for a particular patient at a particular time provided a significant benefit to the pacemaker patient.

However, experience soon indicated that the optimum AVI of the pacemaker for pacing was different than the optimum AVI for sensing. That is, it was found that if an A-pulse was delivered to the atrium, the optimum AVI should be somewhat longer, e.g. 25 milliseconds, than if the AVI was triggered by sensing a P-wave. Hence, it is known in the pacemaker art to generate one AVI in response to generating an A-pulse, and another (shorter) AVI in response to sensing a P-wave. This difference in optimum values has been attributed to intra-atrial conduction delays. That is, depending upon the particular location at which an atrial stimulus (A-pulse) is applied to the atrial tissue (typically in the right atrial appendage), it takes a finite time for this stimulus to reach the primary inter-atrial conduction pathways (internodal tracts) of the heart. Once the stimulus does reach the inter-atrial conduction paths, rapid conduction occurs, resulting in depolarization of the right atrium followed by depolarization of the left atrium. See, e.g., Ausbel et al., "Interatrial Conduction During Cardiac Pacing," *PACE*, Vol. 9, pp. 1026-1031 (Nov/-Dec 1986, Part II); Wish et al., "Importance of Left Atrial Timing in the Programming of Dual-Chamber Pacemakers," *Am. J. of Cardiol.*, Vol. 60, pp. 556-571 (Sept. 1987); Alt et al., "Different Beneficial AV Intervals with DDD Pacing After Sensed or Paced Atrial Events," *J. of Electrophys.*, Vol. 1, No. 3, pp. 250-256 (1987); and Catania, et al., "AV Delay Latency Compensation," *J. of Electrophys.*, Vol. 1, No. 3, pp. 242-249 (1987). In other words, when the pacemaker applies an A-pulse to the right atrium, such application does not cause instantaneous depolarization of the atria. Rather, the applied stimulus must be transferred through available conduction paths within the right atrium, and between the right and left atria, before atrial depolarization can occur. In contrast, when the pacemaker senses a P-wave, depolarization of the atria is already in process. Thus, it is known in the art for pacemakers to incorporate an automatic shortening of the programmed AVI after a sensed atrial event (P-wave). This automatic shortening attempts to make the effective AV delay (the time from the atrial depolarization to the ventricular depolarization) substantially the same regardless of whether the pacemaker is pacing or sensing. Unfortunately, however, such shortening of the AVI adds to the complexity of the pacemaker circuits, and may not provide the correct amount of shortening for a given patient at all times. This is because, as indicated, the inter-atrial and/or intra-atrial conduction times (latency time) vary greatly from patient to patient, and also vary a great deal for a particular patient at different times. Hence, what is needed is a simple means for automatically adjusting the programmed AVI of a pacemaker to include the latency time of a particular patient, whatever that latency time may be. The present invention advantageously addresses this and other needs.

SUMMARY OF THE INVENTION

In accordance with one aspect of the invention, an implantable pacemaker is provided wherein the pacemaker's programmed AV interval is always measured from the evoked atrial potential (i.e., P-Wave), regardless of whether such evoked atrial potential results from an applied stimulus (pacing) or from a sinus rhythm (natural heartbeat). The length of the AV interval is programmed to a desired value using conventional programming techniques. As the AV interval (AVI) represents the best estimate of the nodal conduction time in the patient's heart as a stimulus travels from the atria to the ventricles, i.e., the AVI represents an estimate of the optimum time between atrial depolarization and ventricular depolarization, by always starting the AVI from the evoked atrial potential, rather than from an applied stimulus (A-pulse), all variability in conduction time due to lead position and specific patient latency is advantageously removed, thereby obviating the need of making adjustments to the AVI in order to compensate for such variations.

In accordance with yet another aspect of the present invention, an implantable pacemaker includes AV timer circuit means for providing a paced AV delay that is automatically adjusted to include patient variations in intra-atrial and inter-atrial nodal conduction time due to lead position and specific patient latency. The AV timer circuit means provides a programmed AV interval, commencing at the generation of an atrial pulse (A-pulse), and resetting to start over again at the occurrence of the evoked atrial potential. In the preferred embodiment, the evoked atrial potential is monitored from a ring electrode of a bipolar lead relative to the pacemaker can (case), i.e., ring to case. Other configurations are also possible for monitoring the evoked potential, e.g., bipolar (tip electrode to ring electrode) or unipolar (tip electrode to case). The length of the AV interval is programmed to a desired value using conventional programming techniques. By starting the AV timer circuit means from the paced atrial stimulus, and restarting it from the evoked atrial potential, all variability in nodal conduction time due to lead position and specific patient latency is removed, thereby obviating the need of having the pacemaker make adjustments to the AV interval. The paced AV delay (the time interval from the generation of an atrial stimulus to the generation of a ventricular stimulus) is automatically adjusted to compensate for these variations, while the AV interval (desired time from an atrial depolarization to a ventricular depolarization) remains at the desired programmed value.

In accordance with another aspect of the invention, a rate responsive pacemaker is provided having similar AV timer circuit means, but the programmed AV interval is shortened (or otherwise adjusted) during periods of exercise or other physical activity to mimic changes in AV nodal conduction that occur during such periods of activity.

One embodiment of the invention may thus be characterized as a programmable implantable pacemaker that includes: (1) means for generating an atrial stimulus; (2) first sensing means for sensing an evoked atrial potential of a patient's heart, this evoked atrial potential representing a depolarization of the atria of the heart in response to either a natural atrial depolarization or a paced atrial depolarization, the paced depolarization resulting from the application of an atrial stimulus to the heart by the pacemaker's atrial stimulus generating means; (3) timing means responsive to both the applied atrial stimulus and the evoked atrial potential for generating an AV interval, the AV interval having a duration equal to a prescribed programmed value, and the AV interval, once started by the applied atrial stimulus, being restarted by the occurrence of the evoked atrial potential so that the overall delay from the application of the atrial stimulus to the conclusion of the AV interval includes the prescribed programmed value plus the time interval between the applied atrial stimulus and the evoked atrial potential; (4) means for generating a ventricular stimulus at the conclusion of the AV interval; and (5) means for selectively programming selected operating parameters of the pacemaker, these operating parameters including the programmed value of the AV interval.

Another embodiment of the invention may be viewed as a system for automatically adjusting the AV delay of a programmable implantable pacemaker. The AV delay of such a pacemaker comprises the maximum time allowed by the pacemaker between application of an atrial stimulus or intrinsic (sinus) atrial activity and the application of a ventricular stimulus. The system in accordance with this embodiment of the invention comprises: (a) timer means for generating a prescribed AV interval, this prescribed AV interval commencing with the application of a trigger signal to the timer means; (b) means for sensing an evoked atrial potential evidencing depolarization of the atria, this sensed depolarization resulting from either the application of the atrial stimulus or intrinsic atrial activity; (c) means for generating an atrial stimulus in the absence of intrinsic atrial activity; (d) means for generating the trigger signal of the timer means upon generating an atrial stimulus and upon sensing intrinsic atrial activity, so that in the presence of intrinsic atrial activity the timer means commences its prescribed AV interval upon sensing the evoked atrial potential, and so that in the absence of intrinsic atrial activity the timer means commences its prescribed AV interval upon generating the atrial stimulus and restarts the prescribed AV interval upon sensing the evoked atrial potential resulting from application of the atrial stimulus; and (e) means for generating a ventricular stimulus at the conclusion of the prescribed AV interval. Advantageously, such system automatically adjusts the AV delay to be equal to the prescribed AV interval in the presence of intrinsic atrial activity (i.e., when a P-wave naturally occurs), and to be equal to the prescribed AV interval plus the time interval between application of an atrial stimulus and a resulting evoked atrial potential in the absence of intrinsic atrial activity (i.e., when a P-wave results from application of a stimulation pulse).

A still further embodiment of the invention comprises a method of adjusting the AV delay of a programmable implantable pacemaker to include the latency time between application of an atrial stimulus and the resulting evoked atrial potential. The AV delay of the pacemaker, in accordance with this method, is defined as the maximum time allowed by the pacemaker between application of an atrial stimulus and the application of a ventricular stimulus. The method includes the steps of: (a) starting an AV timer upon the generation of an atrial stimulus, the pacemaker including means for programming a desired value of an AV interval into this AV timer; (b) sensing an evoked atrial potential, this evoked atrial potential evidencing depolarization of the atria, this sensed depolarization resulting from either the application of the atrial stimulus in step (a) or intrinsic atrial activity (i.e., naturally occurring P-waves); (c) restarting the AV timer upon the sensing of the evoked atrial potential in step (b) in the event the AV timer was initially started by the generation of an atrial stimulus in step (a), or starting the AV timer upon the sensing of the evoked atrial potential in the event of intrinsic atrial activity; and (d) generating a ventricular stimulus at the conclusion of the AV interval. Advantageously, the use of this method causes the AV delay to be equal to the AV interval plus the latency time interval between application of an atrial stimulus and a resulting evoked atrial potential when an atrial stimulus is applied. If no atrial stimulus is applied, the AV delay is simply equal to the AV interval.

It is a feature of the present invention to provide a circuit for use in a programmable pacemaker that includes means of automatically adjusting the AV delay of the pacemaker to include whatever latency time may exist for a given patient at a given time.

It is a further feature to provide such a circuit that maintains the time interval between an atrial depolarization (whether a paced or intrinsic depolarization) and a subsequent paced ventricular depolarization to a desired value, which value may be programmably changed as required to suit the needs of the patient.

It is another feature of the invention to provide such adjustment means using simple circuitry that consumes little power and requires only a very small space, thereby enhancing the implantability of the circuit.

Yet another feature of the invention is to provide such an automatic AV adjustment means in a circuit that can be used in either a conventional demand dual chamber pacemaker or a rate-responsive dual chamber pacemaker.

BRIEF DESCRIPTION OF THE DRAWINGS

The above and other aspects, features and advantages of the present invention will be more apparent from the following more particular description thereof, presented in conjunction with the following drawings wherein:

FIG. is a typical ECG-type waveform illustrating the normal heart rhythm;

FIG. 5 is a block diagram illustrating one embodiment of a circuit used to automatically adjust the paced AV delay of a dual chamber pacemaker in accordance with the present invention; and FIGS. 6A and 6B are timing diagrams illustrating the operation of the circuitry shown in FIG. 5 for intrinsic and paced operation, respectively.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
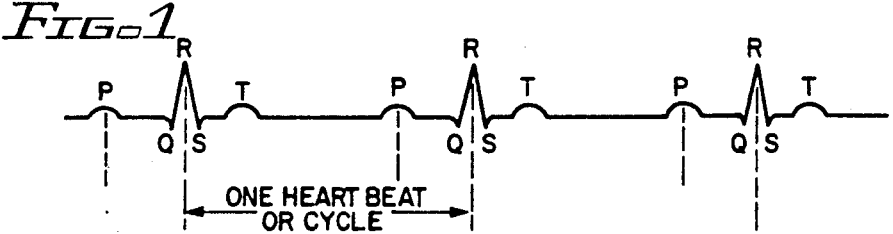

Referring to FIG. 1, there is shown a typical ECG-type waveform illustrating the normal operation and cardiac cycle of a heart. Such waveforms may be obtained using conventional skin-electrode ECG techniques. Alternatively, intracardiac ECG features of modern pacemakers may provide similar ECG information through the use of the telemetry features of such pacemakers. Beginning at the left of the waveform there is shown a P-wave. This P-wave represents the electrical activity coincident with the depolarization of the atria of the heart. Depolarization of the atria is accompanied by contraction of the atria, thereby allowing blood to be pushed from the atria into the ventricles of the heart. While those skilled in the art will recognize that depolarization and contraction are not necessarily simultaneous events, they will be assumed to be simultaneous events for purposes of this patent application, and the terms "depolarization" and/or "contraction" are meant to be synonymous.

A short time subsequent to the generation of the P-wave, the QRS complex appears, representing the depolarization of the ventricles. The time period between the P-wave and the QRS wave (often referred to as simply an R-wave) is a very important time interval in the operation of the heart because it represents the time needed for the blood to flow from the atria into the ventricles. The R-wave is followed by a T-wave, which wave represents the electrical activity associated with the repolarization of the ventricles. As known to those skilled in the art, the ventricles do most of the work in pumping the blood throughout the body. Typically, one heart beat or heart cycle is measured as the time interval between succeeding R-waves, simply because the R-wave typically represents the easiest of the waves to identify and measure. A heart beat could, of course, be measured relative to any point within the heart cycle, such as between succeeding T-waves or P-waves.

The important point to recognize is that a certain rhythm or synchrony must occur if the heart is to function efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricle. If the depolarization of the atria or ventricles do not occur naturally, then a pacemaker may be employed to provide stimulation pulses to these respective heart chambers, in order to trigger the required depolarization/contraction at the appropriate time periods of the heart cycle.

Figure 2A:
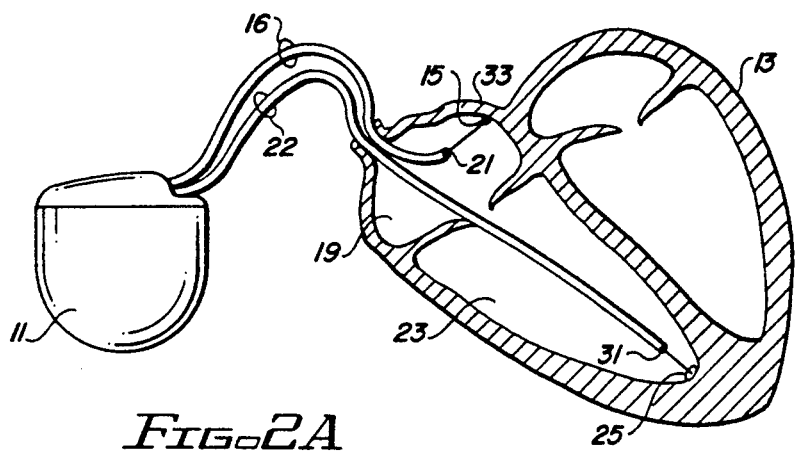
FIG. 2A is a simplified representation of the heart showing the manner in which a pacemaker is connected thereto through insertion of bipolar leads into both the right atrium and the right ventricle.

FIG. 2A shows a simplified diagram of one way an implanted pacemaker 11 may make electrical contact with the heart 13. Two (2) bipolar leads 16, 22 are being directed into a separate chamber of the right heart. A bipolar lead comprises a single filar that includes two (2) electrically insulated conductors. A first conductor of bipolar lead 16 is electrically connected to a distal tip 15. A second conductor is electrically connected to a conductive ring electrode 21 approximately one inch from the distal tip 15. The distal tip 15 is typically placed in a cavity of the right atrium 19 referred to as the atrial appendage 33. Similarly, a bipolar lead 22 having a distal tip 25 and a conductive ring electrode 31 are placed in the apex of the right ventricle 23. Alternately, the leads may be unipolar leads or other multipole leads, all of which are known in the art.

Figure 2B:
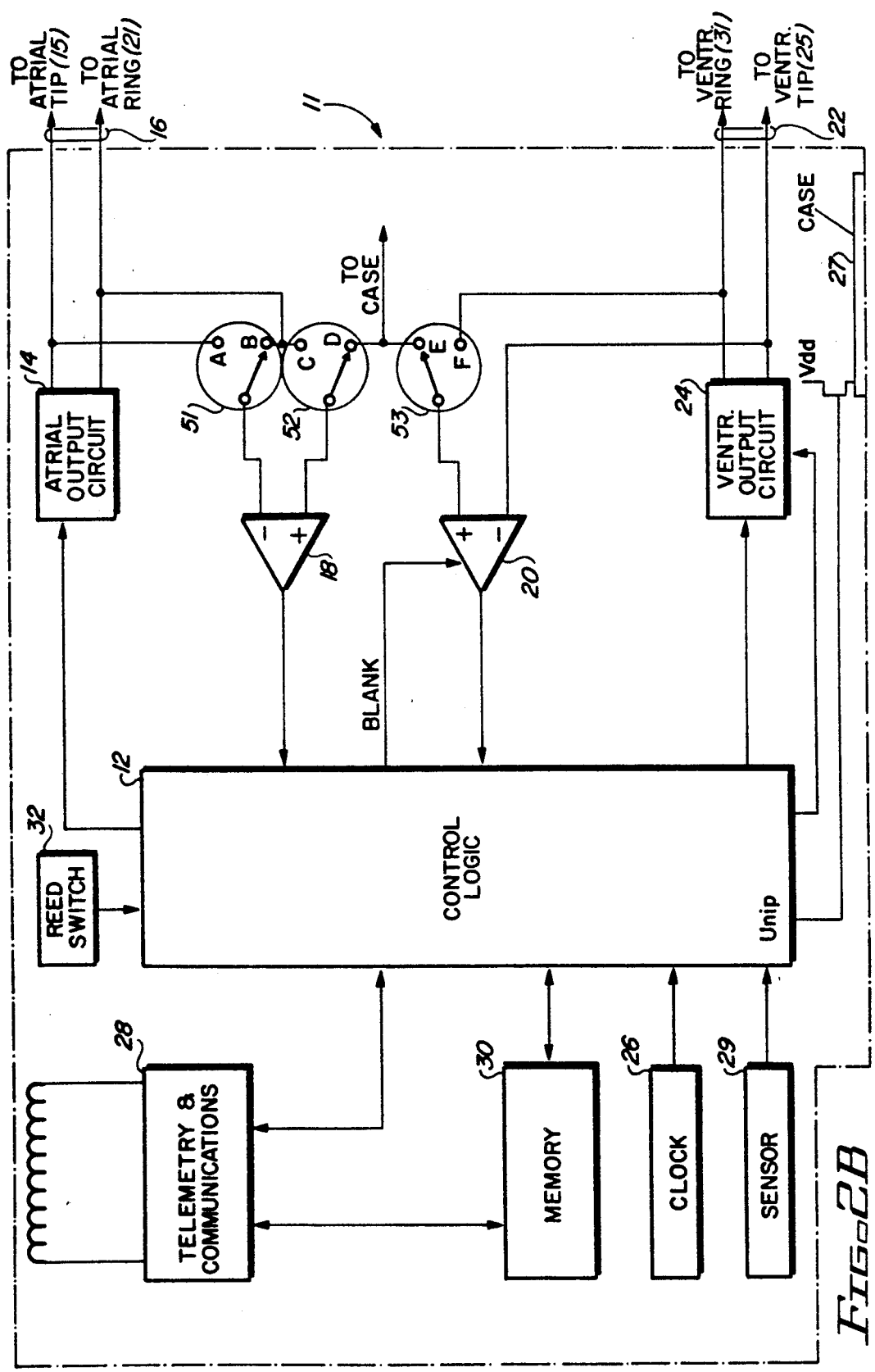
FIG. 2B is a block diagram of the preferred embodiment of an implantable, programmable, dual-chamber pacemaker, and illustrates one manner in which the evoked atrial potential may be monitored through the use of a ring electrode of an atrial lead.

Referring next to FIG. 2B, a block diagram of an atrial tracking dual-chamber pacemaker 11 adapted to operate in accordance with the preferred embodiment of the present invention is illustrated. Control logic 12 generates the appropriate timing sequences and stimulation pulses for delivery to the heart. Stimulation pulses are delivered to the right atrium of the heart through an atrial drive amplifier 14 to the atrial lead 16 connected to the atrial tip electrode 15. Similarly, stimulation pulses are delivered to the right ventricle of the heart through a ventricular drive amplifier 24 to the ventricular lead 22 connected to the ventricular tip electrode 25.

The pacemaker preferably includes configuration programmability by incorporating switches S1, S2 and S3. This means that even though a bipolar lead is used, as shown in FIG. 2B, the stimulation pulse can be programmably delivered to the heart through the tip electrode with a return path through body tissue to the case electrode (tip to case pacing), through the tip electrode with a return path through the ring electrode (tip-to-ring pacing), or through the ring electrode with a return path through body tissue to the case electrode (ring-to-case pacing). That is, any desired combination of bipolar, unipolar (tip-to-case), or unipolar (ring-to-case) pacing may be used. Such configuration programmability also applies to sensing, as explained below. Advantageously, all three modes of pacing and sensing are achieved using a conventional bipolar lead.

In the preferred embodiment, an evoked atrial potential (that is, the potential evoked by a stimulus, or, naturally, by the heart) is sensed through the ring electrode for both intrinsic atrial depolarization, often termed sinus or intrinsic P-waves, and paced depolarization often termed paced P-waves. U.S. Pat. No. 4,686,988 provides further details relative to sensing the evoked atrial response through such a ring electrode of a bipolar lead, which patent is incorporated herein by reference. The ring electrode 21, in the preferred configuration shown in FIG. 2B, is connected to the negative input of an atrial sense amplifier 18 by switching switch S1 to position "B", while the case electrode 27 is connected to the positive input of atrial sense amplifier 18 by switching switch S2 to position "D". This sense amplifier 18 monitors both intrinsic and paced P-waves, as sensed between the ring electrode 21 and the case electrode 27, to determine the evoked atrial potential.

However, it should be noted that sensing of intrinsic and paced P-waves is not required to use the same method of sensing for both intrinsic and paced P-waves, nor is it limited to unipolar (ring-to-case) sensing. It is noted that the sensing configuration described above, wherein the evoked atrial potential is sensed unipolar (ring-to-case), is only representative of one of several sensing configurations that could be used to sense the evoked atrial potential. For example, sensing of both intrinsic and paced P-waves can also occur using a conventional unipolar lead (having only a tip electrode) by sensing unipolar (tip-to-case). Sensing of intrinsic and paced P-waves could also occur using a conventional bipolar lead and programming any combination of bipolar (tip-to-ring), unipolar (tip-to-case), or unipolar (ring-to-case), using the following switch settings:

| Atrial Sense Amplifier | S1 | S2 |
|---|---|---|
| Unipolar (tip-to-case) | A | D |
| Unipolar (ring-to-case) | B | D |
| Bipolar (tip-to-ring) | A | C |

Further, a multiple ring electrode lead could be used (having a tip electrode and a plurality of ring electrodes), in which case sensing could occur between any selected combination of electrode pairs. Indeed, as many modern pacing devices have configuration programmability, wherein the device may be programmed to operate so as pace or sense tip-to-case, ring-to-case, tip-to-ring, etc., it is to be understood that the present invention is not limited to sensing both intrinsic or paced P-waves ring-to-case, as shown in FIG. 2B. Rather, any desired combination of bipolar, unipolar (tip-to-case), and unipolar (ring-to-case) may be used to pace, sense intrinsic P-waves, and sense the evoked potential.

Still referring to FIG. 2B, if such sinus atrial activity is sensed, then the control logic 12 inhibits the stimulation pulse provided to the drive amplifier 14 and provides for a tracked ventricular stimulus, or V-pulse, after a predetermined time period (referred to as the AV delay). However, if after a prescribed period of time after the last ventricular event (either an R-wave or a V-pulse), typically referred to as the VA delay or atrial escape interval (AEI), a sinus P-wave has not been sensed, then the control logic 12 causes a stimulation pulse, or A-pulse, to be delivered through the drive amplifier 14, to the atrium. The pulse width and amplitude of this stimulation pulse are controlled by the control logic 12.

In a similar manner, the control logic 12 senses the electrical activity occurring in the right ventricle 23 of the heart through a sense amplifier 20 connected to the ventricular lead 22 having tip electrode 25 in contact with ventricular tissue. If naturally occurring ventricular electrical activity is not sensed within an appropriate AV delay, often referred to as a ventricular escape interval, then the control logic 12 generates a ventricular stimulation pulse (V-pulse) of a prescribed pulse width and amplitude, delivered through the drive amplifier 24, ventricular lead 22 and tip electrode 25, in order to evoke the desired ventricular contraction.

Clock circuitry 26 provides the basic clock signal from which the control logic 12 operates. Telemetry and communications circuitry 28 provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulating pulse. Such control information may also be passed directly to the control logic 12, if desired. Similarly, electrical activity of the heart, as sensed through additional amplifiers (not shown), can be telemetered external to the pacemaker through the telemetry and communications circuitry 28, thereby allowing an attending physician or other medical personnel, e.g., cardiologist, to monitor the activity of the heart without the use of external skin electrodes. A magnetic reed switch 32 is also typically employed with implanted pacemakers in order to control the programmable functions of the device. With a suitable programming apparatus in place, the attending physician or cardiologist can effectuate any desired changes in the operation of the pacemaker by sending appropriate control signals and commands over the telemetry and communications circuitry 28.

In recent years, it has been desirable to make some pacemakers rate responsive, meaning that the heart rate controlled by the pacemaker may increase or decrease in accordance with the sensed physiological needs of the patient. For such a rate-responsive pacemaker, there may also thus be included within the pacemaker 11 a physiological sensor 29. It is the function of the sensor 29, when used, to sense some physiological parameter associated with the patient, which physiological parameter provides some measure of whether the heart rate of the patient should increase or decrease. While the sensor 29 in FIG. 2B is shown as being included inside of the pacemaker 11, it is to be understood that it may be external to the pacemaker and coupled thereto through appropriate leads. A common type of sensor 29 known and used in rate-responsive pacemakers is a piezoelectric crystal mounted inside of the pacemaker that senses the physical activity of the patient. Other types of sensors known in the art measure, e.g., respiration rate, blood oxygen level, blood pH, body temperature, etc. It is also known in the art to use measured time intervals as a physiological parameter, e.g., the R-T interval. As explained below, any of these parameters could be used with a rate-responsive pacemaker that includes the present invention.

Figure 3:
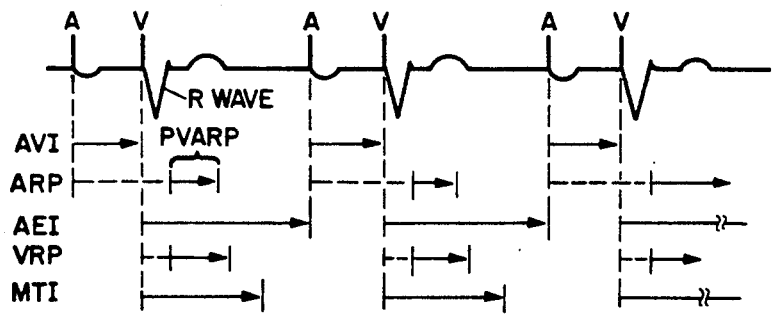
FIG. 3 is a composite timing diagram illustrating how a desired rhythm of the heart is maintained when both atrial and ventricular stimulation pulses are provided to the heart by a dual-chamber pacemaker.

Referring next to FIG. 3, a composite timing diagram illustrating the operation of a typical demand-type, dual-chamber pacemaker, is illustrated. This timing diagram is presented to aid the reader in better understanding the operation of such a pacemaker. In this and other timing diagrams used herein, the stimulation pulses generated by the pacemaker are illustrated as a narrow spike labeled with either an A (for an atrial stimulation pulse) or a V (for a ventricular stimulation pulse). Further, the response of the heart to an applied stimulation pulse is indicated in the figures as having an opposite polarity from that shown in FIG. 1. (FIG. 1 depicts the natural or sinus rhythm of the heart, and thus the heart responds without the application of a stimulation pulse.) This is done to clearly distinguish in the figures naturally occurring events of the heart from pacer-induced (paced) events.

Included in the timing diagram of FIG. 3 are representations of the various timing intervals that are generated by the control logic 12 (FIG. 2B). Many of these time intervals are programmable, meaning that the length of such intervals can be varied by sending appropriate control signals over the telemetry and communications circuitry 28 to the memory circuits 30 of FIG. 2B. As known to those skilled in the electronic arts, there are numerous methods and techniques through which a time interval can be varied. One such technique involves loading an appropriate data word into a prescribed memory location, which data word can in turn be subsequently loaded into an appropriate counter of the control logic 12. A basic clock signal may then be used to clock this counter until the desired count is reached, at which time a terminal count signal (frequently termed a "timed-out" signal) is generated to indicate the end of the desired time interval. By merely changing the value of the data word that is loaded into memory, the length of the time interval can thus be varied or programmed to a desired value.

The time intervals shown in FIG. 3 are indicated by a horizontal line. If the time interval has "timed-out"— that is, if it has reached its terminal count—an arrowhead is placed on the horizontal line, pointing to the point in time at which the time interval terminates. (The horizontal axis of the timing diagrams represents the time axis.) Shown in FIG. 3 are five basic time intervals. These are: (1) the AV interval, or AVI, representing the desired time interval between atrial depolarization and ventricular depolarization (to be distinguished from the AV delay, which for purposes herein is the time interval between an A-pulse and a V-pulse); (2) the atrial refractory period, or ARP, representing the time interval subsequent to the generation of an atrial stimulation pulse or sensed atrial event during which the atrial sensing circuits may be disabled; (3) the atrial escape interval, or AEI, representing the time interval after which, in the absence of naturally occurring atrial or ventricular activity during such interval, an A-pulse is generated and delivered to the atrium (sometimes also referred to as the VA interval); (4) the ventricular refractory period, or VRP, representing the interval during which the ventricular sense amplifier 20 (FIG. 2B) is disabled; and (5) the maximum tracking interval, or MTI, representing the maximum ventricular paced rate.

With the above timing intervals thus defined, the following description of FIG. 3 can be better understood. As indicated previously, FIG. 3 illustrates how a pacemaker is used to maintain a desired rhythm or synchrony of the heart. For the situation shown in FIG. 3, it is assumed that the heart being stimulated cannot provide its own atrial or ventricular contractions at a suitable rate, and that the pacemaker must therefore provide the stimulation pulses required to maintain the desired heart rate. Accordingly, an atrial stimulation pulse A is provided in order to invoke a contraction of the atrium. This event triggers both the A-V interval, AVI, and the atrial refractory period, ARP. In prior art pacemakers, the ARP disabled the atrial sense amplifier 18 and blanked its operation for the duration of the ARP. (The ARP is divided into an absolute refractory portion, shown as the dashed line portion of the ARP horizontal line, and a relative refractory portion, shown as a solid line. The distinction between absolute and relative refractory portions of the ARP is not relevant to the present invention.) Use of the ARP is generally necessary to prevent the atrial sense circuits from sensing ventricular events. Further, because the atrial sense amplifier is typically connected to the same electrode as used in pacing, the large stimulation pulse used to stimulate the atrium thus also appears at the input of the sense amplifier 18, thereby possibly saturating the atrial sense amplifier. Hence, unless the amplifier 18 is blanked or otherwise rendered inoperative during this time, the saturated amplifier may not recover from such saturation in sufficient time to perform its sensing function. In accordance with one embodiment of the present invention, however, the sensing amplifier 18 is not connected to the tip electrode 15. Hence, the ARP shown in FIG. 3 need not be utilized, at least not to the extend shown or suggested by FIG. 3. That is, for a sense amplifier connected only to the ring electrode 21, as shown in FIG. 2B, no blanking period (or only a very short blanking period) is required. However, if an additional sense amplifier were to be employed, connected to the tip electrode 15, as shown, e.g., in U.S. Pat. No. 4,686,988, then an ARP as shown in FIG. 3 would generally be employed for such additional sense amplifier.

Continuing with the explanation of FIG. 3, at the termination of the AVI, a ventricular stimulation pulse, V, is generated and applied to the heart. This stimulation pulse causes the ventricle to contract, as indicated by the inverted R-wave. The generation of the ventricular stimulation pulse, or V-pulse, also triggers the beginning of the atrial escape interval, or AEI; the ventricular refractory period, or VRP; the post-ventricular atrial refractory period (PVARP); and the maximum tracking interval, or MTI. Note, unlike the atrial sense amplifier 18, the ventricular sense amplifier 20 is connected to the tip electrode 25 through the same ventricular lead 22 through which the V-pulses are provided. Hence, the VRP is needed to blank the operation of the amplifier 20 for an appropriate time. At the conclusion of the AEI (or V-A interval), there having been no P-waves sensed, an A-pulse is generated in order to produce a contraction of the atrium, thereby initiating the next cycle of the heart. Thus, the events previously described begin again and the cycle repeats itself, with a V-pulse being generated after the AVI subsequent to the A-pulse, and an A-pulse being generated after the AEI subsequent to the V-pulse. In this manner, the desired rhythm of the heart is maintained.

Figure 4:
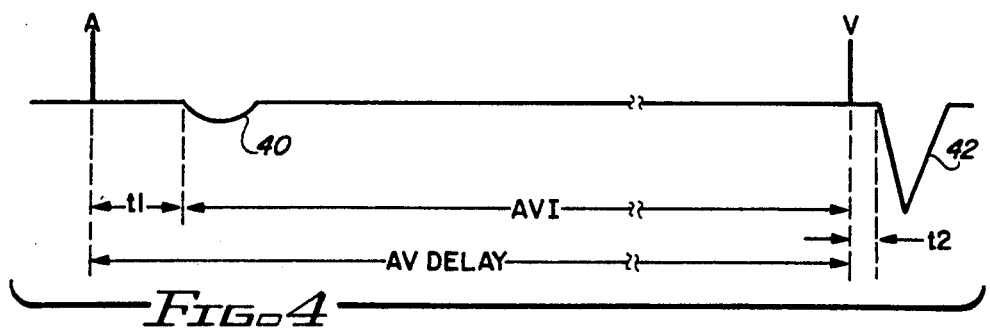
FIG. 4 is an expanded view of a portion of the timing diagram of FIG. 3 and illustrates the latency between application of an atrial stimulus and the evoked atrial potential.

Turning next to FIG. 4, an expanded timing diagram of a portion of one paced cardiac cycle is shown. FIG. 4 illustrates the latency conduction time that exists when an A-pulse is applied to the heart in order to evoke depolarization. As shown in FIG. 4, the A-pulse does not produce an instantaneous contraction of the atrium. Rather, it takes a finite time, t1, before the atrial tissue depolarizes in response to the A-pulse. This finite time t1 represents the latent conduction time that it takes for the A-pulse to travel from its point of application (at the tip electrode 15) to the appropriate locations within the atrial tissue responsible for producing an atrial depolarization. The time t1 varies as a function of numerous factors, including the location of the atrial tip electrode 15 within the atrium, any drugs being administered to the patient, the level of activity of the patient, etc. After this time t1, the atria depolarize, as evidenced by the inverted P-wave 40. This depolarization is used by the present invention to start the AVI, or (as explained below) to restart the AVI. At the conclusion of the AVI, assuming no R-waves have occured, the V-pulse is generated. Note that the AVI, as shown in FIG. 4, represents the time interval between the atrial depolarization and the application of the V-pulse. There may also be a latent conduction time, t2, between application of the V-pulse and the ventricular depolarization, represented by the inverted R-wave 42. However, this ventricular latency time t2 is generally very small compared to the overall V-A interval, and for most purposes (relevant to operation of the pacemaker) this time t2 may be safely ignored. Thus, the AVI shown in FIG. 4 comes very close to being equal to the actual atrial-to-ventricular depolarization time of the heart.

Note also from FIG. 4 that the AV delay shown comprises the latency time t1 plus the AVI. Because the latency time t1 may represent a significant portion, e.g., 5-50%, of the overall AV delay for a typical patient, and because it is the actual atrial-to-ventricular depolarization time that a pacemaker should ideally control, there is thus a need to include within the pacemaker some means for automatically adjusting the AV delay so that it accounts for the latency time t1, including all of the variations of such time as might exist for a given patient under different conditions. The present invention advantageously addresses this need through the use of a circuit as shown in FIG. 5.

FIG. 5 is a block diagram illustrating one embodiment of a portion of the control logic of FIG. 2B used to practice the present invention. As shown in FIG. 5, such control logic functionally includes an AV timer circuit 50 and a VA timer circuit 52. A timed-out (T.O.) signal is generated by each timer at the conclusion of a programmed interval. The programmed interval for the AV timer 50 is stored in an assigned portion of the memory 30 (FIG. 2B). From the memory 30 it is selectively transferred in conventional manner to a holding register 30a, or equivalent device, for use by the AV timer 50. The AV timer 50 receives the programmed AV interval from the register 30a over a load terminal or line, identified in FIG. 5 as "L". (For some device types, it may be possible to transfer the programmed AV interval directly from its storage location within the memory 30 to the AV timer 50, in which case there is no need for the register 30a. In such instance, the block 30a shown in FIG. 5 may be functionally considered as part of the memory 30 shown in FIG. 2B.) The AV timer 50 is triggered or started by application of an appropriate signal to one of its trigger terminals, labeled "T". As shown in FIG. 5, there are two signals that can trigger or start the AV timer: (1) an evoked atrial potential as sensed by sense amplifier 18; or (2) a timed-out (T.O.) signal generated by the VA timer 52. At any time, the AV timer 50 may be disabled, or halted, by application of an appropriate signal to its enable/disable terminal, labeled "H". For the configuration shown in FIG. 5, the sensing of ventricular activity, e.g. an R-wave, by the ventricular sense amplifier 20' functionally causes the AV timer 50 to be disabled or halted.

In a similar manner, the programmed interval for the VA timer 52 is stored in an assigned portion of the memory 30, from where it is selectively transferred, in conventional manner, to a holding register 30b, or equivalent device, for use by the VA timer 52. From the register 30b (which may also be functionally considered as part of the memory 30 for some device types, as explained above), this programmed VA interval is loaded into the VA timer 52 over a load terminal or line, "L". The VA timer 52 is triggered or started by one of two possible signals applied to its trigger inputs, "T". These two possible signals are: (1) a T.O. signal from the AV timer 50; or (2) a signal from the sense amplifier 20' indicating sensed ventricular activity. As further shown in FIG. 5, the output of the atrial sense amplifier 18 is also connected to the "H" terminal of the VA timer 52, thus causing the VA timer to be halted or disabled upon the sensing of an evoked atrial potential by the atrial sense amplifier 18.

It is noted that the purpose of halting or disabling the timers 50 or 52 is to inhibit the generation of a V-pulse or A-pulse. Numerous techniques could be used, in addition to halting or disabling the timers, to perform this inhibiting function.

As explained previously in connection with FIG. 2B, the atrial sense amplifier 18 is, in the preferred embodiment, connected to a ring electrode 21 in the atrium, and is thus adapted to sense an evoked atrial potential within the atrium. (Other configurations, as explained previously, could also be employed to sense the evoked potential.) Similarly, a ventricular sense amplifier 20' is adapted to sense ventricular activity over a lead 22'. If desired, the sense amplifier 20' may also be connected to a ring electrode (not shown) in the ventricle via the lead 22', thereby allowing the sense amplifier 20' to sense the evoked ventricular potential in a manner similar to the way in which amplifier 18 senses the evoked atrial potential. (Alternatively, the lead 22' may simply be connected to the same lead 22 used with the ventricular pulse amplifier 24, as shown in FIG. 2B.)

The atrial sense amplifier 18, as well as ventricular sense amplifier 20', may be of conventional design. It is preferred that appropriate frequency, time domain and/or amplitude filtering be employed within such amplifiers, as disclosed, e.g., in the above-referenced patent. Such filtering helps assure that noise is not sensed as an evoked atrial or ventricular potential. Amplitude filtering typically involves the use of a threshold level above which the input signal must go before it is accepted as a valid evoked potential. Frequency filtering limits valid signals to a prescribed bandwidth. Time domain filtering limits valid signals to fall within a prescribed time window, i.e., to have at least a minimum width but not exceeding a maximum width.

The AV timer 50 and VA timer 52 may also be of conventional design. In a preferred embodiment, these timer circuits are digital timers. Such timers include a register that is configured as a counter and adapted to be clocked by a suitable clock signal (having a known period) so as to count up/down to or from the prescribed time value (the programmed AV or VA intervals). Numerous digital integrated circuits are commercially available that can perform this counting function. Alternatively, an appropriate counting circuit can be readily fashioned using conventional flip flops and logic gates that will also perform this function. Moreover, analog timer circuits are also known in the art that can be used to generate a programmed delay.

An atrial pulse amplifier 14, when triggered, causes an atrial pulse to be generated and delivered to the atrium over lead 16. Similarly, a ventricular amplifier 24, when triggered, causes a ventricular pulse to be generated and delivered to the ventricle over lead 22. These pulse amplifiers 14 and 24 may be of conventional design.

It is to be emphasized that which is shown in FIG. 5 is functional in nature. Those skilled in the electronic and pacemaker arts can readily fashion appropriate logic circuitry, using commercially available digital and analog components, to realize a circuit that performs the functions described, and that does so taking into consideration all of the other varied and many considerations that must be taken into account in the design of an implantable pacemaker, which considerations are omitted herein because they are not needed to understand the present invention.

It is desired, of course, that all of the circuits within the pacemaker 11 be included on the same chip, or at least on a small number of chips, thereby allowing the size of the pacemaker to be kept as small as possible. It is also desirable that the circuits be realized using a circuit technology, such as CMOS or NMOS, that consumes as little power as possible, thereby allowing the useful life of the pacemaker's battery to last as long as possible. The techniques for combining a desired circuit design on a CMOS chip, using, e.g., gate arrays and/or VLSI designs, are known in the art and will not be described herein.

Referring next to the timing diagrams of FIGS. 6A and 6B, and with continued reference to FIG. 5, the operation of the circuit shown in FIG. 5 will be explained. In FIG. 6A, an evoked atrial potential is shown as an intrinsic P-wave 60. This P-wave 60 is labeled EPW, meaning "evoked P-wave". The EPW 60 is sensed by amplifier 18, causing the AV timer 50 to begin or start its programmed AV interval. The operation of the AV timer 50 is depicted in FIG. 6A as a logic signal that goes high and remains high for so long as the AV timer 50 is carrying out its function of timing out the programmed AV interval. At the conclusion of the programmed AV interval, a timed-out (T.O.) signal pulse 61 is generated. This T.O. pulse 61 is applied to the input of pulse amplifier 24, causing a V-pulse 62 to be generated. The time interval between the EPW 60 and the V-pulse 62 is thus the AV delay of the pacemaker. For the intrinsic EPW 60 shown in FIG. 6A, i.e., for the naturally occurring P-wave (not paced), the AV delay is thus equal to the programmed AV interval. If ventricular activity is sensed while the AV timer is timing out, such sensing halts operation of the AV timer 50, or uses other means to prevent the V-pulse 62 from being generated, in accordance with conventional demand pacemaker operation.

As seen in FIG. 5, it is noted that the T.O. pulse 61 is also applied to the VA timer 52, causing the programmed VA delay to begin timing out. If atrial activity is sensed while the VA timer 52 is timing out, such sensing halts operation of the VA timer, or uses other means to prevent an A-pulse from being generated, in accordance with conventional demand pacemaker operation. As the present invention is concerned primarily only with generation of the AV delay, and not the VA delay, such operation is not shown in the timing diagrams of FIGS. 6A and 6B. However, it is to be understood that a similar timing operation occurs, with the difference that the VA delay is much longer than the AV delay, and that the present invention could be used (if desired) to automatically adjust the VA delay as well as the AV delay.

Referring next to FIG. 6B, the operation of the circuit of FIG. 5 will be explained for paced operation, i.e., for a situation where an A-pulse 64 is generated and delivered to the atrium in order to produce a desired atrial contraction. In response to an A-pulse 64, the atrium contracts, causing an evoked atrial potential, shown as inverted EPW 66 in FIG. 6B. As described above in connection with the description of FIG. 4, there is a latency time t1 between application of the A-pulse 64 and the occurrence of the EPW 66. The generation of the A-pulse causes the AV timer 50 to begin its programmed AV interval. (Actually, as seen in FIG. 5, it is the T.O. signal from the VA timer 52, in anticipation of generating an A-pulse, that triggers the AV timer 50. However, except for very small circuit delays associated with the response time of the pulse amplifier 14, the T.O. signal from the VA timer and the generation of the A-pulse may be considered as occurring at essentially the same time.) However, after the latency time t1, the EPW 66 is sensed. This sensing causes the AV timer 50 to restart the programmed AV interval. At the conclusion of the programmed AV interval, a T.O. pulse 67 occurs, which pulse causes a V-pulse 68 to be generated. The time interval between when the AV timer was first started, i.e., at the occurrence of the A-pulse 64, and the generation of the V-pulse 68 thus comprises the AV delay of the pacemaker. However, this AV delay is different from the AV delay shown in FIG. 6A. The AV delay in FIG. 6B is automatically adjusted to include the programmed AV interval plus the latency time t1.

Still referring to FIG. 6B, the operation of the circuit of FIG. 5 will be explained for a situation where the latency time changes. If the latency time t1 increases, for example, an EPW 66' (shown with dotted-lines) occurs later. In such instance, the AV timer 50 is restarted at the sensing of the EPW 66', causing a T.O. pulse 67' to be generated at the conclusion of the programmed AV interval thereafter, which in turn causes V-pulse 68' to be generated. The overall AV delay of the pacemaker is thus adjusted to include the programmed AV interval plus this increased latency time. Advantageously, during operation of the pacemaker, the interval between the evoked atrial potential (whether resulting from a natural P-wave or a paced P-wave) and the application of a V-pulse will always be equal to the programmed AV interval, while the AV delay of the pacemaker will be automatically adjusted to include whatever latency time may exist.

An added advantage associated with the present invention is that a pacemaker incorporating the automatic AV delay adjustment circuitry as described above need not be unduly complicated. Rather, the circuits of such pacemaker can be functionally as simple as shown in FIG. 5, thereby greatly simplifying the pacemaker circuits over that which has been utilized in the prior art to provide one AV delay when sensing and an increased AV delay when pacing. Moreover, such simplified pacemaker provides significantly improved performance, as the AV delay of the pacemaker will always be adjusted to include whatever latency times may be present in a particular patient at a particular time.

Further, it is to be emphasized that the present invention may be used just as easily with a rate responsive pacemaker, as with a non-rate-responsive pacemaker. As previously described, a rate-responsive pacemaker is one wherein the basic timing intervals of the pacemaker, e.g. the AV interval and the VA interval, are adjusted as a function of a sensed physiological parameter, such as the patient's physical activity, indicative of whether the patient's heart rate should increase or decrease. If the sensed physiological parameter indicates the heart rate should increase, for example, such as when the patient is exercising, the programmed VA and AV intervals may be shortened an appropriate amount in order to cause the pacemaker to deliver stimulation pulses at a faster rate, when needed (i.e., on demand). As the sensed physiological parameter indicates the heart rate should decrease, then the programmed VA and AV intervals are lengthened an appropriate amount, at an appropriate rate of change, in order to gradually bring the paced heart rate back to a rest rate. (Reference may be made to U.S. Pat. Nos. 4,856,523 and 4,712,555 for a more complete description of the operation of different types of rate-responsive pacemakers.) Advantageously, the present invention may be readily used with such a rate-responsive pacemaker because it is the programmed AV interval (and/or the programmed VA interval), that is changed as a function of the sensed physiological parameter. Thus, in accordance with the teachings of this invention, the appropriate rate-responsive AV interval, regardless of its value at any instant of time as changed by the sensed physiological parameter, is always included in the pacemaker's AV delay, as is the particular latency time of the patient at that time, thereby maintaining the appropriate physiologically-determined AV interval as the time between the atrial depolarization and the application of a ventricular stimulus.

While the invention herein disclosed has been described by means of specific embodiments and applications thereof, numerous modifications and variations could be made thereto by those skilled in the art without departing from the scope of the invention set forth in the claims.

What is claimed is:

1. A system for automatically compensating for latency conduction time in a programmable implantable pacemaker, the latency conduction time being the time interval between a stimulus to the heart and the responsive evoked potential, the system comprising:

means for generating a first stimulus in the absence of intrinsic activity;

means for sensing an evoked potential evidencing depolarization of one of the ventricles or the atrium of the heart, the sensed depolarization resulting from either the application of the first stimulus or intrinsic activity;

timer means for generating a prescribed pacing interval, the prescribed pacing interval commencing with the application of a trigger signal to the timer means;

means for generating the trigger signal of the timer means upon generating the first stimulus and upon sensing the evoked potential, so that in the presence of intrinsic activity the timer means commences its prescribed pacing interval upon sensing the intrinsic activity, and so that in the absence of intrinsic activity the timer means commences its prescribed pacing interval upon generating the first stimulus and restarts the prescribed pacing interval upon sensing the evoked potential resulting from application of the first stimulus; and means for generating a second stimulus at the conclusion of the prescribed pacing interval;

whereby the time interval between the generation of the first and second stimulus is equal to the sum of the prescribed pacing interval and the interval between the first stimulus and the resulting evoked potential in the absence of intrinsic activity.

2. A programmable implantable pacemaker comprising:

means for generating an atrial stimulus;

first sensing means for sensing an evoked atrial potential of a patient's heart, the evoked atrial potential representing a depolarization of the atria of the heart in response to either a natural atrial depolarization or a paced atrial depolarization, the paced atrial depolarization resulting from the application of an atrial stimulus to the heart by the atrial stimulus generating means;

timing means responsive to both the applied atrial stimulus and the evoked atrial potential for generating an AV interval, the AV interval having a maximum duration equal to a prescribed programmed value, the AV interval, once started by the applied atrial stimulus, being restarted by an occurrence of an evoked atrial potential so that the overall delay from the application of the atrial stimulus to the conclusion of the AV interval includes the prescribed programmed value plus the time interval between the applied atrial stimulus and the evoked atrial potential;

means for generating a ventricular stimulus at the conclusion of the AV interval; and means for selectively programming selected operating parameters of the pacemaker, the operating parameters including the programmed value of the AV interval.

3. The pacemaker as set forth in claim 2, wherein the first sensing means includes:

a case electrode;

a bipolar lead having a distal end and a proximal end, a tip electrode at the distal end being connected to a first proximal terminal at the proximal end by a first conductor, and a ring electrode spaced apart from the tip electrode at the distal end being connected to a second proximal terminal at the proximal end by a second conductor, the bipolar lead being insertable within the heart so that the ring electrode is proximate desired atrial tissue;

a sense amplifier for sensing an electrical potential between first and second input terminals thereof, the first input terminal being connected to a selected one of the tip electrode and the ring electrode, and the second input terminal being connected to a selected one of the ring electrode and the case electrode;

whereby the sense amplifier senses the electrical potential between a selected one of the tip-and-ring electrodes, the tip-and-case electrodes, or the ring-and-case electrodes.

4. The pacemaker as set forth in claim 2, wherein the atrial stimulus generating means includes:

pulse generator means for generating an atrial stimulation pulse having a pulse width and amplitude as determined by at least one of the programmed operating parameters of the pacemaker; and an output amplifier for directing the atrial stimulation pulse to the first proximal terminal of the bipolar lead, the output amplifier having an electrical return path through a selected one of the case electrode of the pacemaker or the ring electrode of the bipolar lead;

whereby the atrial stimulation pulse may be applied to the heart at the location within the heart where the distal electrode contacts cardiac tissue, with a return electrical path being selectively provided through body tissue to either the case electrode of the pacemaker or the ring electrode of the bipolar lead.

5. The pacemaker as set forth in claim 4 further including:
second sensing means for sensing an evoked ventricular potential; and
means for inhibiting the application of the atrial stimulation pulse to the heart in the event the second sensing means senses an evoked ventricular potential prior to the termination of the AV interval.

6. The pacemaker as set forth in claim 2 further including:
means for sensing a physiological parameter indicative of the need to change the heart rate; and
means for changing the programmed value of the AV interval as a function of the sensed physiological parameter.

7. A system for automatically adjusting the AV delay of a programmable implantable pacemaker to compensate for latency conduction time, the AV delay comprising the maximum time allowed by the pacemaker between application of an atrial stimulus or intrinsic atrial activity and the application of a ventricular stimulus, the system comprising:
timer means for generating a prescribed AV interval, the prescribed AV interval commencing with the application of a trigger signal to the timer means;
means for sensing an evoked atrial potential evidencing depolarization of the atria, the sensed depolarization resulting from either the application of the atrial stimulus or intrinsic atrial activity;
means for generating an atrial stimulus in the absence of intrinsic atrial activity;
means for generating the trigger signal of the timer means upon generating an atrial stimulus and upon sensing intrinsic atrial activity, so that in the presence of intrinsic atrial activity the timer means commences its prescribed AV interval upon sensing the evoked atrial potential, and so that in the absence of intrinsic atrial activity the timer means commences its prescribed AV interval upon generating the atrial stimulus and restarts the prescribed AV interval upon sensing the evoked atrial potential resulting from application of the atrial stimulus; and
means for generating a ventricular stimulus at the conclusion of the prescribed AV interval, whereby the AV delay comprises the AV interval in the presence of intrinsic atrial activity, and the AV delay comprises the AV interval plus the time interval between application of an atrial stimulus and a resulting evoked atrial potential in the absence of intrinsic atrial activity.

8. The automatic adjustment system as set forth in claim 7, wherein the means for sensing an evoked atrial potential includes:
a first electrode positioned to provide the atrial stimulus;
a second electrode positioned to sense atrial depolarization, the second electrode being separate from the first electrode;
a case electrode; and
a sense amplifier electrically connected to the second electrode and the case electrode, the sense amplifier providing an output signal indicative of an evoked atrial potential whenever the sensed atrial depolarization exhibits a prescribed criterion, such as an amplitude above a prescribed level.

9. The automatic adjustment system as set forth in claim 8, wherein the first and second electrodes comprise the tip and ring electrodes, respectively, of a bipolar lead.

10. The automatic adjustment system as set forth in claim 7, wherein the pacemaker further includes means for programmably changing the value of the prescribed AV interval to a desired value.

11. The automatic adjustment system as set forth in claim 10, wherein the pacemaker further includes:
physiological sensor means for sensing a physiological parameter; and
means for automatically changing the value of the prescribed AV interval as a function of the sensed physiological parameter.

12. The automatic adjustment system as set forth in claim 10, wherein the pacemaker further includes:
means for sensing a ventricular depolarization; and
means for inhibiting the ventricular stimulus generating means if a ventricular depolarization sensed during the prescribed AV interval.

13. A system for automatically adjusting the VA delay of a programmable implantable pacemaker, the VA delay comprising the maximum time allowed by the pacemaker between application of an ventricular stimulus or intrinsic ventricular activity and the application of a subsequent atrial stimulus, the system comprising:
timer means for generating a prescribed VA interval, the prescribed VA interval commencing with the application of a trigger signal to the timer means;
means for sensing an evoked ventricular potential evidencing depolarization of the ventricles, the sensed depolarization resulting from either the application of the ventricular stimulus or intrinsic ventricular activity;
means for generating a ventricular stimulus in the absence of intrinsic ventricular activity;
means for generating the trigger signal of the timer means upon generating a ventricular stimulus and upon sensing intrinsic ventricular activity, so that in the presence of intrinsic ventricular activity the timer means commences its prescribed VA interval upon sensing the evoked ventricular potential, and so that in the absence of intrinsic ventricular activity the timer means commences its prescribed VA interval upon generating the ventricular stimulus and restarts the prescribed VA interval upon sensing the evoked ventricular potential resulting from application of the ventricular stimulus; and
means for generating an atrial stimulus at the conclusion of the prescribed VA interval;
whereby the VA delay comprises the VA interval in the presence of intrinsic ventricular activity, and the VA delay comprises the VA interval plus the time interval between application of a ventricular stimulus and a resulting evoked ventricular potential in the absence of intrinsic ventricular activity.

14. A method of adjusting the AV delay of a programmable implantable pacemaker to automatically include any latency time between application of an atrial stimulus and the resulting evoked atrial potential, the AV delay comprising the maximum time allowed by the pacemaker between application of an atrial stimulus and the application of a ventricular stimulus, the method comprising:
  (a) starting an AV timer upon the generation of an atrial stimulus, the pacemaker including means for programming a desired value of an AV interval into the AV timer;
  (b) sensing an evoked atrial potential, the evoked atrial potential evidencing depolarization of the atria, the sensed depolarization resulting from either the application of the atrial stimulus in step (a) or intrinsic atrial activity;
  (c) restarting the AV timer upon the sensing of the evoked atrial potential in step (b) in the event the AV time was initially started by the generation of an atrial stimulus in step (a), or starting the AV timer upon the sensing of the evoked atrial potential in the event of intrinsic atrial activity;
  (d) generating a ventricular stimulus at the conclusion of the AV interval;
  whereby the AV delay comprises the AV interval pulse the time interval between application of an atrial stimulus and a resulting evoked atrial potential when an atrial stimulus is applied, and the AV delay comprises the AV interval when intrinsic atrial activity occurs.

15. The method set forth in claim 14 further including inhibiting the generation of the ventricular stimulus in step (d) in the vent intrinsic ventricular activity is sensed during the time the AV timer is performing its timing function.

16. The method set forth in claim 14 further including sensing a physiological parameter indicative of a need to change the heart rate controlled by the pacemaker, and changing the prescribed AV interval as a function of the sensed physiological parameter.

* * * * *